(12) United States Patent
Pacetti et al.

(10) Patent No.: US 8,263,107 B2
(45) Date of Patent: Sep. 11, 2012

(54) FUNCTIONALIZED CHEMICALLY INERT POLYMERS FOR COATINGS

(75) Inventors: Stephen Dirk Pacetti, San Jose, CA (US); Syed Faiyaz Ahmed Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/186,202

(22) Filed: Jul. 19, 2011

(65) Prior Publication Data

US 2011/0274738 A1 Nov. 10, 2011

Related U.S. Application Data

(63) Continuation of application No. 11/178,196, filed on Jul. 8, 2005, now Pat. No. 8,021,676.

(51) Int. Cl.
*A61F 2/00* (2006.01)
(52) U.S. Cl. .................................................. 424/423
(58) Field of Classification Search ........................ None
See application file for complete search history.

(56) References Cited

U.S. PATENT DOCUMENTS

| | | | |
|---|---|---|---|
| 6,017,741 | A | 1/2000 | Keogh |
| 6,120,587 | A | 9/2000 | Elfersy et al. |
| 7,244,443 | B2 | 7/2007 | Pacetti |
| 8,021,676 | B2 | 9/2011 | Pacetti et al. |
| 2005/0266038 | A1 | 12/2005 | Glauser |
| 2007/0100078 | A1 | 5/2007 | Li et al. |
| 2011/0274734 | A1 | 11/2011 | Pacetti et al. |

FOREIGN PATENT DOCUMENTS

| | | |
|---|---|---|
| DE | 35 23 615 | 1/1987 |
| EP | 1 477 192 | 11/2004 |
| WO | WO 93/05081 | 3/1993 |
| WO | WO 2005/107828 | 11/2005 |
| WO | WO 2006/039152 | 4/2006 |
| WO | WO 2007/008408 | 1/2007 |

OTHER PUBLICATIONS

International Search Report for PCT/US2006/025055, filed Jun. 26, 2006, mailed Jan. 19, 2007, 16 pgs.
Fujimoto et al., "Ozone-induced graft polymerization onto polymer surface", J. of Polymer Science, Part A: Polymer Chemistry vol. 31, No. 4, pp. 1035-1043 (1993).
Liu et al., "Synthesis, characterization and electrochemical properties of poly(methyl methacrylate)-grafted-poly(vinylidene fluoride-hexafluoropropylene) gel electrolytes", Solid State Ionics 150, pp. 317-326 (2002).
Matsumura et al., "Surface modification of poly (ethylene-co-vinyl alcohol) (EVA) Part 1. Introduction of carboxyl groups and immobilization of collagen", J. of Biomed. Mat. Research vol. 50, No. 4, pp. 512-517 (2000).
Wang et al., "Synthesis, characterization and anti-fouling properties of poly(ethylene glycol) grafted poly(vinylidene fluoride) copolymer membranes", Journal of Materials Chemistry, 11:783-789 (2001).
Ying et al., "Synthesis and Characterization of Poly(acrylic acid)-graft-poly(vinylidene fluoride) Copolymers and ph-SensitiveMembranes", Macromolecules, 35:673-679 (2002).
Young et al., "Preparation of cross-linked hyaluronic acid film using 2-chloro-1-methylpyridinium iodide or water-soluble 1-ethyl-(3,3-dimethylaminopropyl) carbodiimide", J. Biomat. Sci. Polym Ed. 15(6) pp. 767-80, Abstract 1 pg. (2004).

*Primary Examiner* — Paul Dickinson
(74) *Attorney, Agent, or Firm* — Squire Sanders (US) LLP

(57) ABSTRACT

Provided herein are methods for functionalizing a polymer for forming a coating and coatings and devices formed thereof or for functionalizing a coating or device surface including an polymer.

8 Claims, No Drawings

FUNCTIONALIZED CHEMICALLY INERT POLYMERS FOR COATINGS

CROSS-REFERENCE TO RELATED APPLICATION

This is a continuation application of U.S. application Ser. No. 11/178,196, filed Jul. 8, 2005, now U.S. Pat. No. 8,021,676 the teaching of which is incorporated herein in its entirety by reference.

BACKGROUND OF THE INVENTION

1. Field of the Invention

This invention generally relates to functionalized polymers (e.g., chemically inert polymers) for coating or forming an implantable device.

2. Description of the Background

Inert polymers such as fluoropolymers and others have been used to form coatings on an implantable device or an implantable device. While some of these polymers can have good properties, e.g., the ability to control drug release rate, good biocompatibility, good mechanical integrity, inertness, or processability, it is often desirable to modify these polymers to alter their drug permeability or to functionalize them to attach moieties for pro-healing, thromboresistance, or biobeneficiality. Generally, a coating or surface is considered biobeneficial when it confers some biological benefit, i.e. thromboresistance, non-fouling, anti-inflammatory, or platelet resistant, without the release of a pharmacologically active agent.

However, due to these polymers' inertness, it is relatively difficult to modify the polymers. For example, chemical functionalization of poly(vinylidene fluoride-co-hexafluoropropylene) (PVDF-HFP) is possible but requires harsh conditions, e.g., heating the polymer in KOH/MeOH at 60° C. for 4 hours to introduce unsaturation followed by treatment with 98% sulfuric acid at 80° C. for 48 hours to oxidize the unsaturation to introduce hydroxyl and carboxyl groups (e.g., Bottino, A., et al., J. Membrane Sci., 166:23-29 (2000)).

Therefore, there is a need for functionalizing inert polymers under relatively benign conditions. The embodiments described below address such problems and needs.

SUMMARY OF THE INVENTION

Provided herein are methods for functionalizing a polymer (e.g., an inert polymer) for forming a coating or functionalizing a coating or device surface formed of a polymer (e.g., an inert polymer). The polymer can be a fluoropolymer such as poly(vinylidene hexafluoropropylene) (PVDF-HFP). The method of functionalizing the polymer includes activation by ozonation, plasma treatment, UV irradiation, gamma irradiation, and/or electron-beam irradiation of the coating or coating or device surface. The polymer treated by this activation processes can be reduced by a chemical agent to generate a hydroxyl functionalized polymer or coating or device surface or alternatively, can be subjected to polymerization grafting with a thermal free radical polymerizable moiety such as poly(ethylene glycol) acrylate (PEG acrylate), poly(ethylene glycol) methacrylate (PEG methacrylate), 1-vinyl-2-pyrrolidinone (VP), methacryloyl phosphoryl choline, methacryloyloxyethyl phosphoryl choline, 2-hydroxyethyl methacrylate, 3-hydroxypropyl methacrylamide, acrylamide, maleic acid, fumaric acid, or cinnamic acid. One or more biofunctional compound such as RGD peptide, YIGSR peptide, ANP peptide, elastin or an endothelial progenitor cell (EPC) capturing antibody, or combinations thereof can be attached to the thus formed functionalized polymer, or to a coating or device surface formed of a functionalized polymer(s).

The functionalized polymer can form a coating on an implantable device (e.g., a stent), optionally with one or more biocompatible polymer and/or one or more biobeneficial material and/or a bioactive agent. Likewise, the coating on an implantable device (e.g., a stent) whose surface can be functionalized as described herein can optionally include with one or more biocompatible polymers and/or one or more biobeneficial materials and/or a bioactive agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N-1-tetrazolyl)-rapamycin (ABT-578), clobetasol, pimecrolimus, imatinib mesylate, midostaurin, prodrugs thereof, co-drugs thereof, or a combination thereof.

The implantable device can be implanted in a patient to treat, prevent or ameliorate a disorder such as atherosclerosis, thrombosis, restenosis, hemorrhage, vascular dissection or perforation, vascular aneurysm, vulnerable plaque, chronic total occlusion, claudication, anastomotic proliferation of vein or artificial grafts, bile duct obstruction, ureter obstruction, tumor obstruction, or combinations thereof.

DETAILED DESCRIPTION

Provided herein are methods of modifying polymers (e.g., inert polymers) which can be used for forming coatings on implantable devices, or modifying a coating formed of one or more polymers (e.g., inert polymers). The method generally includes treating the inert polymer with an activating condition/process and optionally followed by grafting a functional moiety onto the inert polymer or polymer coating. The activating condition can be, e.g., ozonation, plasma treatment, UV irradiation, gamma irradiation, or electron-beam (e-beam) irradiation. The functional moiety can be any functional species having at least one vinyl group, or double bond.

As used herein, the term "inert polymer" refers to any polymer that maintains its structural integrity when exposed to an activating condition such as ozone, plasma treatment, UV irradiation, gamma irradiation, or e-beam radiation for a period up to, e.g., several hours. Some representative inert polymers described herein include, but are not limited to, poly(vinylidene fluoride), poly(vinyl fluoride), poly(vinylidene fluoride-co-hexafluoropropylene), poly(vinylidene fluoride-co-chlorotrifluoroethylene), poly(vinylidene fluoride-co-ethylene), poly(vinylidene fluoride-co-tetrafluoroethylene), poly(tetrafluoroethylene-co-ethylene), fluoropolymers, parylene C, parylene D, parylene N, ultrahigh molecular weight poly(ethylene) (UHMWPE), poly(imide), and poly(ether ether ketone).

The functionalized polymer can be used to form an implantable device or a coating on the implantable device. The functionalized polymer can be used with a biobeneficial material and optionally with one or more bioactive agents. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N-1-tetrazolyl)-rapamycin (ABT-578), clobetasol, pimecrolimus, imatinib mesylate, midostaurin, prodrugs thereof, co-drugs thereof, or a combination thereof. The implantable device can be implanted in a patient to treat, prevent or ameliorate a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Ozonation

In one aspect of the present invention, a polymer (e.g., an inert polymer) can be subjected to ozonation. Ozonation allows the generation of peroxide moieties attached to the backbone of the polymer (Scheme I). The peroxy moieties can be reduced to hydroxyl groups or, alternatively, the peroxide moiety can serve as a thermal initiator to graft one suitable free radical polymerizable moiety to the polymer (Scheme I):

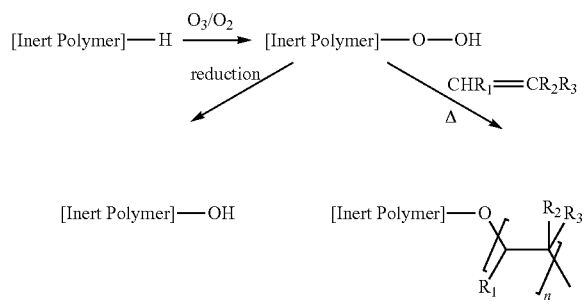

where $R_1$, $R_2$ and $R_3$ are independent organic groups such that $CHR_1=CR_2R_3$ represents a free radical polymerizable moiety and can be any of acrylates, methacrylates, fumarates, cinnamic acid, and maleic acid or derivatives thereof such as poly(ethylene glycol) acrylate (PEG acrylate), poly(ethylene glycol) methacrylate (PEG methacrylate), 1-vinyl-2-pyrrolidinone (VP), methacryloyl phosphoryl choline, methacryloyloxyethyl phosphoryl choline, 2-hydroxyethyl methacrylate, 3-hydroxypropyl methacrylamide, acrylamide, maleic acid, fumaric acid, or cinnamic acid, and n is a positive integer ranging from e.g., 1 to 100,000, 10 to 100,000, 100 to 100,000 or 1,000 to 100,000. Reduction of the peroxy grafted inert polymer can be readily achieved by reacting a reducing agent with the peroxy moieties on the inert polymer. This reduction process converts the peroxy moieties to hydroxyl groups, which increases, amongst other properties, the hydrophilicity, water permeability, water uptake/swelling, and drug release rate of the inert polymer. An example of the reduced peroxy inert polymer is shown below (Scheme IA):

Scheme IA

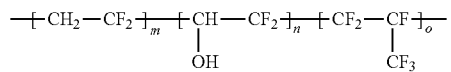

wherein m, n, and o are independently positive integers ranging from e.g., 1 to 100,000, 10 to 100,000, 100 to 100,000 or 1,000 to 100,000.

In some embodiments, the inert polymer is a fluoropolymer such as PVDF-HFP or PVDF, and can be readily ozonated (see, e.g., Wang, P., et al., J. Mater. Chem., 11:783-789 (2001); Liu, Y., Reactive & Functional Polymers, 47:201-203 (2001; and Ying, L., et al., Macromolecules, 35:673-679 (2002)). For example, ozonation of PVDF-HFP proceeds according to Scheme II to form peroxy grafted PVDF-HFP:

Scheme II

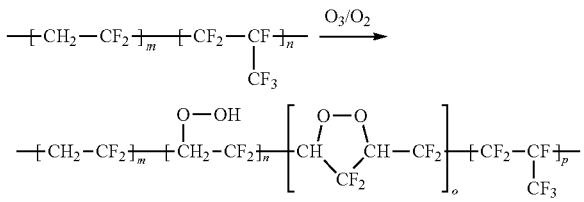

wherein m, n, o and p are independently positive integers ranging from e.g., 1 to 100,000, 10 to 100,000, 100 to 100,000 or 1,000 to 100,000.

The reaction as described in Scheme II can be performed in solution or on a coating or device surface. The peroxide moieties on PVDF-HFP can be reduced, or can serve as a thermal initiator such that functional moieties having a vinyl or double bond group can be grafted onto the polymer (see Scheme I, above, and Schemes III-VI).

Schemes III-IV show some examples of grafting functional moieties onto peroxy fluoropolymers such as PVDF-HFP. In Scheme III, methacryloyloxyethyl phosphoryl choline (MPC) is grafted onto the peroxy grafted PVDF-HFP:

Scheme III

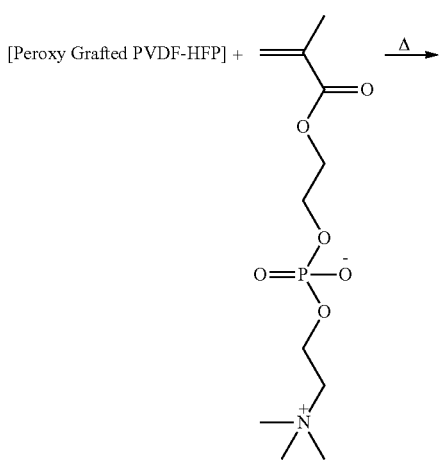

-continued

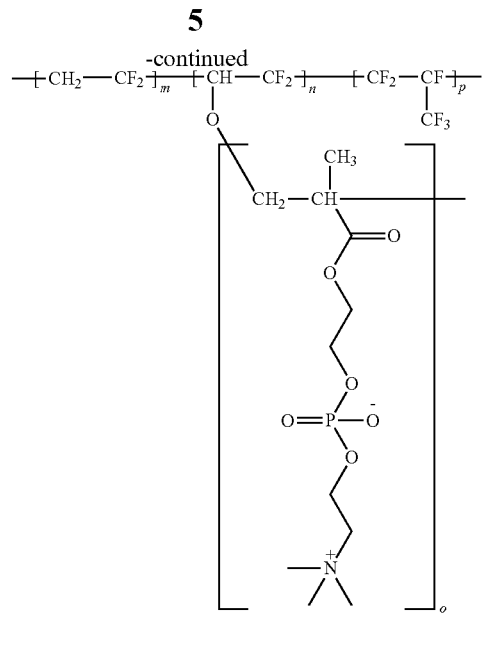

wherein m, n, o and p are independently positive integers ranging from e.g., 1 to 100,000.

Non-fouling moieties can be readily grafted onto a perxoy grafted inert polymer. For example, N-vinyl pyrrolidone can be grafted to the PVDF-HFP according to Scheme IV:

Scheme IV

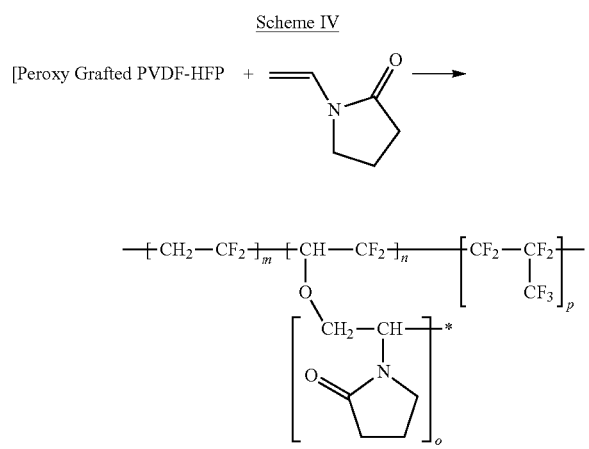

wherein m, n, o and p are independently positive integers ranging from e.g., 1 to 100,000, 10 to 100,000, 100 to 100,000 or 1,000 to 100,000.

As shown in Scheme V, poly(ethylene glycol) (PEG) can be grafted to a peroxy inert polymer via a methacrylate group linked to the PEG, resulting in a brush structure of PEG attached to the inert polymer like PVDF-HFP:

Scheme V

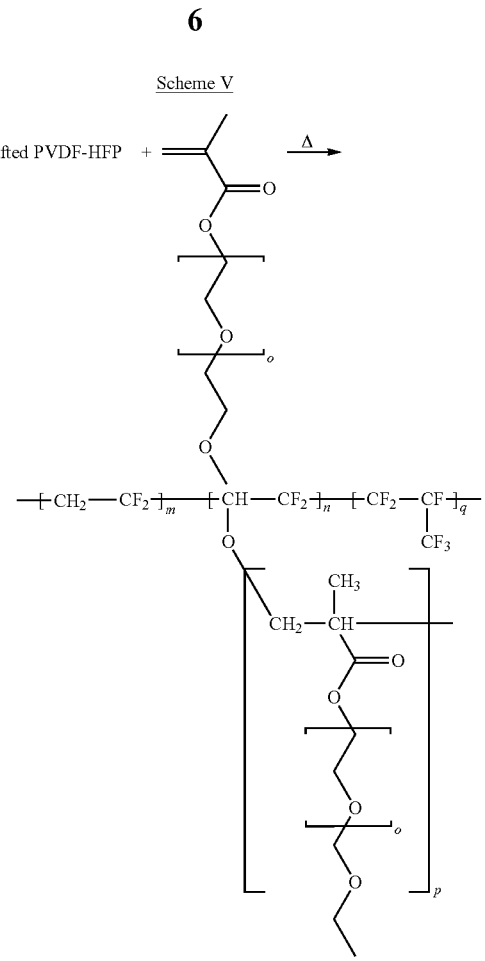

wherein m, n, o, p and q are independently positive integers ranging from e.g., 1 to 100,000, 10 to 100,000, 100 to 100,000 or 1,000 to 100,000.

The PEG-functionalized polymer such as PVDF-HFP can have different PEG content, depending on the molecular weight of the PEG used in the grafting, the stoichiometry of reactive PEG moieties to peroxy groups, and the extent of peroxy groups in the inert polymer.

Other functional moieties such as hydroxyl groups, amino, thiol or carboxyl groups can be attached to an inert polymer. These groups can be used to attach molecules of interest such as biofunctional molecules to the inert polymer (Scheme VI):

Scheme VI

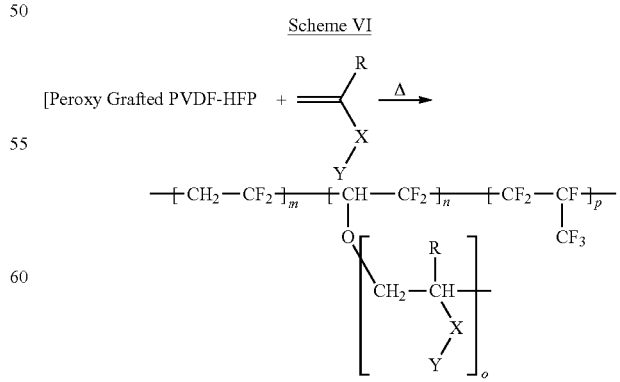

wherein m, n, o and p are independently positive integers ranging from e.g., 1 to 100,000. In Scheme VI, R can be, e.g., H, or a short chain alkyl such as $CH_3$, ethyl, isopropyl, propyl, or n-butyl; X can be O, NH, S, C(O)O, C(O)NH, —OC(O)O—, or C(O)S; and Y can be any groups or moieties having free hydroxyl group(s), amino group(s), or carboxyl group(s) such as —$CH_2CH_2NH_2$, —$CH_2CH_2CH_2NH_2$, —$(OCH_2CH_2)_nNH_2$, —$CH_2CH_2OH$, —$CH_2CH_2CH_2OH$, —$(OCH_2CH_2)_nOH$, —$CH_2CH_2COOH$, —$CH_2CH_2CH_2COOH$, or —$(OCH_2CH_2)_nCOOH$. Scheme VII shows PVDF-HFP grafted with amino groups:

Scheme VII

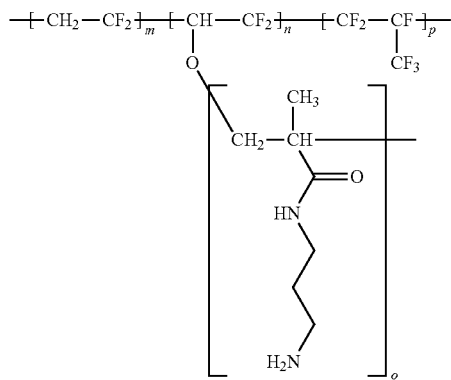

wherein m, n, o and p are independently positive integers ranging from e.g., 1 to 100,000, 10 to 100,000, 100 to 100,000 or 1,000 to 100,000.

The biofunctional molecules that can be attached to an inert polymer via hydroxyl, carboxyl, thiol or amino functionalities can be, for example, peptides, proteins, a drug molecule or other hemocompatible agent, non-fouling, anti-inflammatory, or pro-healing molecules or agents. For example, hydroxyl groups can be used to attach other molecules of interest, including biofunctional molecules, to the inert polymer by treating the hydroxyl inert polymer with an agent such as 1-cyano-4-dimethylamino pyridinium tetrafluoroborate (CDAP), which acts essentially like cyanogen bromide, activating the hydroxyl groups. Subsequent treatment with a molecule of interest such as hyaluronic acid (HA) functionalized with a linking agent, such as adipic dihydrazide, will attach the molecule of interest (e.g., HA) to the inert polymer such as PVDF-HFP. Other methods of attaching the molecule of interest to the inert polymer via any of the hydroxyl, carboxyl, thiol or amino functionalities are well documented in the art, some of which are described in U.S. application Ser. No. 10/857,141, the teachings of which are incorporated herein by reference.

The peroxy moieties formed on the inert polymer may be reduced to hydroxyl groups. The hydroxyl groups can be used to bind bioactive agents. For example, the amino groups of peptides, proteins, RGD peptides, endothelial cell adhesion molecules (ECAMs), and YIGSR peptides may be coupled to hydroxyl groups using chemistries known to those skilled in the art including coupling by CDAP, cyanogen bromide, carbonyl diimidazole, diacid chlorides, or diisocyanates or via conversion of the hydroxyl to a leaving group such as triflate or p-toluenesulfonate followed by nucleophilic addition.

In some embodiments, the ozonation can be carried out on a finished coating of an inert polymer. For example, the coating can be exposed to ozone, e.g., ozone in solution, to functionalize the coating or device surface with peroxy moieties. The peroxy functionalized surface can then be exposed to a solution of a functional moiety that is free radical polymerizable monomer(s), e.g., a monomer having vinyl group(s), and heated. For example, a stent coated with an inert polymer can be immersed in an aqueous solution of polymerizable monomer, which can be heated at, e.g., 60° C. for a short period of time (e.g., several seconds to several minutes) to decompose the initiator to initiate polymerization. The coating or device surface can thus be grafted with the functional moiety. After the grafting, the surface can be rinsed with de-ionized (DI) water to remove unreacted monomers. In the case where the coating is a drug-delivery coating having a drug, the ionic strength of the solution can be increased to mitigate release of the drug into the solution, if any.

In some embodiments, the inert polymer or polymer coating can be activated by other processes and then subjected to grafting with one or more functional moieties. These activating processes are capable of activating an inert polymer or the coating or device surface formed of an inert polymer to generate radicals and can be, for example, plasma activation, UV irradiation, gamma irradiation, or e-beam irradiation. It can be advantageous to carry out the plasma process using air, oxygen, or oxygen containing gaseous species in order to create peroxy moieties. Otherwise, the plasma activation can create active free radials, which can be used to initiate polymerization if the radicals can be preserved or contacted with the coupling moieties before the free radicals are quenched. Similarly, it can be advantageous to carry out the irradiation processes in an air, oxygen, or oxygen containing atmosphere to facilitate formation of peroxy species.

In some other embodiments, the inert polymer or a coating of the inert polymer activated as described above can be subjected to the following grafting processes to attach various biofunctional or bioactive molecules to the inert polymer or coating. For example, a stent with a Solef™ (PVDF-HFP) polymer coating, with or without a drug such as everolimus, can be first subjected to ozonolysis, plasma (e.g., inert argon plasma activation, air, oxygen, or $CO_2+HO_2$ plasma activation), UV irradiation, gamma irradiation, and/or e-beam irradiation, followed by inert argon plasma treatment, inert argon and $CO_2$ plasma treatment, $CO_2$ and $H_2O$ plasma treatment, and/or $CO_2$ and $H_2O$ plasma, and then followed by immersion into a solution that includes PEG acrylate, VP (1-vinyl-2-pyrrolidinone), methacryloyl phosphoryl choline, and/or another free radical polymerizable biobeneficial moiety.

In some embodiments, the coating of an inert polymer such as a Solef™ polymer can be subjected to ozonolysis, a first plasma, UV irradiation, gamma irradiation, and/or e-beam irradiation, followed by $CO_2+H_2O$ plasma treatment without any immersion step described above. Alternatively, the coating of an inert polymer such as a Solef™ polymer can be subjected to ozonolysis, a first plasma, UV irradiation, gamma irradiation, or e-beam irradiation, followed by $CO_2+H_2O$ plasma treatment and then by immersion into an organic acid solution such as a maleic acid, fumaric acid, or cinnamic acid solution, and then optionally reaction with peptides such as RGD peptide, YIGSR peptide, ANP peptide, and/or elastin or a protein such as the endothelial progenitor cell (EPC) capturing antibody by reductive amination or carbodiimide chemistry (see, Young, J. J., J Biomater Sci Polym Ed. 15(6): 767-80 (2004)).

The plasma treatment can be controlled/tuned by duration of the treatment, plasma pressure, plasma power, plasma frequency, bias between substrate and plasma electrode(s), plasma precursor partial pressure, and combinations thereof, and the immersion step can be controlled/tuned by solution concentrations, solution pH, temperature, and ionic strength of the solution, which can be readily worked out by one of ordinary skill in the art.

Other Biocompatible Polymers

In some embodiments of the present invention, the functionalized polymer may form a coating and/or bioerodable implantable device with one or more other biocompatible polymers. Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanoate), poly(4-hydroxyheptanoate), poly(4-hydroxyoctanoate) and copolymers including any of the 3-hydroxyalkanoate or 4-hydroxyalkanoate monomers described herein or blends thereof, polyesters, poly(D,L-lactide), poly(L-lactide), poly(L-lactide-co-D,L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly (anhydrides), poly(tyrosine carbonates), poly(tyrosine arylates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide)/poly(lactic acid) (PEO/PLA), polyalkylene oxides such as poly(ethylene oxide), poly(propylene oxide), poly (ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), poly(lactic acid-co-PEG) (PLA-PEG), poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-L-lactic acid), poly(D, L-lactic acid-co-glycolic acid), or poly(L-lactic acid-co-glycolic acid), respectively.

Biobeneficial Material

In some embodiments, the functionalized polymer may form a coating or a bioerodable implantable device optionally with one or more biobeneficial materials. The combination can be mixed, blended, or coated in separate layers. The biobeneficial material useful in the coatings described herein can be a polymeric material or non-polymeric material.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly(ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly(ethylene glycol) (PEG) or polyalkylene oxide e.g., poly(ethylene oxide).

Other Bioactive Agents

In some embodiments, the functionalized polymer may form a coating or bioerodable device with one or more other bioactive agents. These bioactive agents can be any agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, anti-mitotic, antibiotic, antiallergic, antioxidant as well as cytostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include 40-epi-(N-1-tetrazolyl)-rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include pimecrolimus, imatinib mesylate, midostaurin, alpha-interferon, bioactive RGD, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects, and greater than the level at which non-therapeutic results are obtained. The dosage or concentration of the bioactive agent can depend upon factors such as the particular circumstances of the patient; the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, the bioerodable implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, closure devices for patent foramen ovale, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating or device of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. In accordance with some other embodiments of the invention, bioabsorbable or non-degradable devices can be formed of a material containing the polymer of Formula I. The material can be the polymer of Formula I or a polymer blend containing the polymer of Formula I with one or more biocompatible polymers, optionally with a biobeneficial material and/or a bioactive agents, which are defined above.

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a coating on an implantable device, comprising
    (a) subjecting a polymer to ozonation to form a peroxy grafted polymer,
    (b) subjecting the peroxy grafted polymer to a process of reduction or $CO_2+H_2O$ plasma treatment followed by immersion into an organic acid solution to generate a functionalized polymer,
    (c) attaching a biofunctional compound to the functionalized polymer, and
    (d) forming a coating on the implantable device comprising the polymer prior to ozonation or forming a coating on the implantable device comprising the functionalized polymer with the biofunctional compound attached thereon,
    wherein the organic acid is selected from the group consisting of maleic acid, fumaric acid, cinimanic acid, and a combination thereof,
    wherein the biofunctional compound is an RGD peptide, YIGSR peptide, ANP peptide, elastin, an endothelial progenitor cell (EPC) capturing antibody, an endothelial cell adhesion molecule (ECAM), or combinations thereof.

2. The method according to claim 1, wherein the polymer is poly(vinylidene fluoride-co-hexafluoropropene) (PVDF-HFP).

3. A stent comprising a coating formed by the method according to claim 1.

4. A stent comprising a coating formed by the method according to claim 2.

5. The stent according to claim 3, wherein the coating further comprises a bioactive agent selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and a combination thereof.

6. The stent according to claim 4, wherein the coating further comprises a bioactive agent selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, and a combination thereof.

7. A method of treating a disorder in a patient comprising implanting in the patient the stent of claim 3, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

8. A method of treating a disorder in a patient comprising implanting in the patient the stent of claim 4, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *